United States Patent [19]

Kotani et al.

[11] Patent Number: 5,518,905

[45] Date of Patent: May 21, 1996

[54] METHOD FOR PRODUCING L-3,4-DIHYDROXYPHENYLALANINE BY PRECIPITATION OF ANHYDROUS CRYSTALS

[75] Inventors: Takuya Kotani; Katsuo Iizumi; Makoto Takeuchi, all of Kawasaki, Japan

[73] Assignee: Ajinomoto Co., Inc., Tokyo, Japan

[21] Appl. No.: 281,695

[22] Filed: Jul. 28, 1994

[30] Foreign Application Priority Data

Jul. 30, 1993 [JP] Japan ................ 5-190583

[51] Int. Cl.⁶ ........................ C12P 13/22
[52] U.S. Cl. ........................ 435/108; 435/847
[58] Field of Search ................ 435/108, 847

[56] References Cited

U.S. PATENT DOCUMENTS

| | | | |
|---|---|---|---|
| 3,813,317 | 5/1974 | Benoiton et al. | 195/29 |
| 5,338,672 | 8/1994 | Tsuchida | 435/108 |

FOREIGN PATENT DOCUMENTS

| | | |
|---|---|---|
| 2091396 | 1/1972 | France . |
| 1960524 | 7/1970 | Germany . |
| 2152548 | 4/1972 | Germany . |
| 4031975 | 8/1974 | Japan . |
| 0049250 | 5/1975 | Japan . |
| 0049249 | 5/1975 | Japan . |
| 2000288 | 1/1987 | Japan . |

OTHER PUBLICATIONS

Perry's Chemical Engineer's Handbook, pp. 19–24 to 19–40, Publishers: McGraw Hill, Inc., 1984.
Kirk–Othmer Encyclopedia of Chemical Technology, vol. 7, Publishers: John Wiley & Sons, Inc. pp. 243–285, 1979.
Patent Abstracts of Japan, vol. 17, No. 482 (C–1105)(6111), Sep. 2, 1993, JP-A-5 123177, May 21, 1993.

Primary Examiner—Michael G. Wityshyn
Assistant Examiner—S. Saucier
Attorney, Agent, or Firm—Oblon, Spivak, McClelland, Maier & Neustadt

[57] ABSTRACT

A method for producing L-3,4-dihydroxyphenylalanine comprising contacting microorganism cells having β-tyrosinase activity with catechol, pyruvic acid and ammonium ion or with catechol and L-serine, at a temperature lower than 25° C. in the presence of anhydrous crystals of L-3,4-dihydroxyphenylalanine. L-3,4-dihydroxyphenylalanine formed from said contacting precipitates as anhydrous crystals in the reaction mixture, and the thus-precipitated anhydrous crystals can be collected. According to the method of the present invention, crude crystals of L-3,4-dihydroxyphenylalanine having a high purity may be obtained at a high yield of recovery.

17 Claims, No Drawings

METHOD FOR PRODUCING L-3,4-DIHYDROXYPHENYLALANINE BY PRECIPITATION OF ANHYDROUS CRYSTALS

BACKGROUND OF THE INVENTION

1. Field of the Invention

The present invention relates to a method for producing L-3,4-dihydroxyphenylalanine (hereinafter referred to as L-DOPA). L-DOPA has been popularly used as for treating Parkinson's disease.

2. Description of the Background

Previously, L-DOPA has been produced synthetically starting from vanillin. In addition, other methods for producing L-DOPA, using an enzymes and microorganisms, have been investigated. For example JP-B 48-34237 (the term "JP-B" as used herein means an "examined Japanese patent publication") describes a method for producing L-DOPA from catechol, pyruvic acid and ammonium ion using β-tyrosinase. JP-B 47-22275 describes a method for producing L-DOPA from catechol and L-serine and other amino acids also using β-tyrosinase. JP-B 62-24076 describes a method for producing L-DOPA from dihydroxycinnamic acid and ammonium ions using ammonia lyase. JP-B 47-19033 and JP-B 47-14915 describe methods for producing L-DOPA from L-phenylalanine or L-tyrosine, using oxygenase. JP-B 58-18475 describes a method for producing L-DOPA from 3,4-dihydroxyphenylpyruvic acid using transaminase.

There are two types of L-DOPA crystals, monohydrated crystals and anhydrous crystals. Monohydrated crystals of L-DOPA are needle-like crystals, while anhydrous crystals of L-DOPA are tetragonal crystals. JP-B 49-41188 describes a method of purifying L-DOPA by crystallizing needle-like crystals of L-DOPA from an aqueous L-DOPA solution containing impurities at a low temperature not higher than 30° C. followed by heating them at a temperature not lower than 30° C. so as to convert them into tetragonal crystals by polymorphic transition and separating the thus-converted tetragonal crystals from the solution. According to this method, L-DOPA is crystallized as needle-like crystals whereby the color substances and other impurities that have been in the crude L-DOPA obtained in the production step are effectively removed. Afterwards, the needle-like crystals are separated and then converted into tetragonal crystals of pure L-DOPA by polymorphic transition.

JP-A 5-123177 (the term "JP-A" as used herein means an "unexamined published Japanese patent application") describes the production and accumulation of an extremely high concentration of L-DOPA by improving a method of producing L-DOPA which uses β-tyrosinase. According to this method, L-DOPA is produced and accumulated in the reaction mixture at a concentration higher than the solubility of L-DOPA in the liquid. However, when the reaction is conducted at low temperatures, the crystals precipitated are monohydrated crystals and are thus difficult to separate and recover. On the other hand, when the reaction is conducted at high temperatures, anhydrous crystals of L-DOPA are precipitated. Unfortunately, many unfavorable side products are formed in the reaction system reducing the yield of crystals obtained. Accordingly, it is desirable to find a method of producing L-DOPA inexpensively and more efficiently than known conventional methods of producing L-DOPA.

SUMMARY OF THE INVENTION

Accordingly, one object of the present invention is to provide a method of producing L-DOPA inexpensively and more efficiently than known conventional methods of producing L-DOPA.

The present inventors have now achieved this goal with their discovery of a method comprising contacting microorganism cells having β-tyrosinase activity with catechol, pyruvic acid and ammonium ion or with catechol and L-serine, at a temperature lower than 25° C. in the presence of anhydrous crystals of L-DOPA. The L-DOPA precipitates as anhydrous crystals in the reaction mixture at temperatures lower than 25° C. These precipitated anhydrous crystals may easily be separated and recovered.

Various other objects, features and attendant advantages of the present invention will be more fully appreciated as the same becomes better understood from the following detailed description.

DETAIL DESCRIPTION OF THE PREFERRED EMBODIMENTS

A first embodiment of the method of the present invention (L-DOPA) comprises producing L-DOPA by contacting microorganism cells having a β-tyrosinase activity, or a product to be obtained by processing them, with catechol, pyruvic acid and ammonium ion or with catechol and L-serine at a temperature lower than 25° C. under conditions where anhydrous crystals of L-DOPA are present in the reaction mixture, precipitating anhydrous crystals of L-DOPA in the reaction mixture, and collecting said anhydrous crystals of L-DOPA.

Suitable microorganisms which can be used in accordance with the present invention may be any microorganism having β-tyrosinase (tyrosine-phenol lyase, EC 4.1.99.2) activity. Microorganisms belonging to the genus Erwinia are preferred as they have high activity. *Erwinia herbicola* (ATCC 21433) and *Erwinia herbicola* (ATCC 21434) which have been deposited in the American Type Culture Collection, 12301 Parklawn Dr., Rockville, Md. 20852, on Oct. 28, 1969 are particularly preferred.

In addition, also usable in the present invention are mutants or transformants having improved L-DOPA productivity which are produced by mutating the above-mentioned microorganisms or by transforming them by genetic engineering techniques, etc.

The microorganisms of the present invention may be cultured in a medium containing carbon sources, nitrogen sources, inorganic salts and other nutrient substances. Suitable carbon sources include glycerol, fumaric acid, saccharides, etc. Suitable nitrogen sources include ammonium sulfate, amino acids, etc. Suitable inorganic salts include potassium phosphate, magnesium sulfate, ferrous sulfate, manganese sulfate, zinc sulfate, etc. Other suitable nutrient substances include hydrolysates of soybean protein, amino acids, etc.

As β-tyrosinase is considered to be an adaptive enzyme, it is preferred to culture the above-mentioned microorganisms while adding tyrosine or tyrosine substitutes to the medium. Suitable tyrosine substitutes include isomers and derivatives of tyrosine. In this manner, the expression of the β-tyrosinase activity in the cells can be augmented to give improved results. In addition, it is also preferred to add vitamin $B_6$ and the like to the medium so as to elevate the β-tyrosinase activity to be expressed in the cells.

Cultivation of the microorganisms of the present invention is suitably conducted at temperatures within the range of from 15° C. to 45° C. The culture is suitably kept from slightly acidic to slightly alkaline, preferably at a pH of from 6.0 to 8.5. The cultivation is suitably continued for 10 to 72 hours. After the microorganisms being cultured have grown to the stationary phase, incubation may be continued for a further 6 to 24 hours while the pH of the culture is maintained within a range from 7.0 to 8.3 to obtain microorganism cells having a higher β-tyrosinase activity (allowed U.S. Ser. No. 08/036,268) (see JP-A 5-123177).

The microorganisms having a β-tyrosinase activity are then contacted with catechol, pyruvic acid and ammonium ion or with catechol and L-serine.

To obtain L-DOPA by contacting the culture of these microorganisms with catechol, pyruvic acid and ammonium ion, the ammonium ion can be any ammonium salt including ammonium acetate, ammonium chloride, ammonium sulfate, ammonium nitrate, ammonium phosphate and ammonium salts of any organic acid. Preferably, ammonium chloride is used as the source of ammonium ion, since the production rate for L-DOPA is more than twice as fast as that in the reaction using other ammonium salts.

Suitable concentrations of catechol, pyruvic acid, ammonium ion and serine in the reaction mixture are 0.01–0.1M, 0.01–2M, 0.1–1M, and 0.01–0.2M, respectively.

The catechol, pyruvic acid an ammonium ion can be added into the reaction mixture in the whole quantity at the beginning of the reaction or in divided portions during the reaction. Preferably, solution of catechol, pyruvic acid and ammonium ion is added continuously or intermittently into the reaction mixture so that the concentration of catechol is maintained at 1.0% wt. (0.09M) or less.

The cultured medium containing the microorganisms may be used as the reaction medium. Alternatively, isolated cells can be used. Suitably, 1 to 10% of the wet weight of the reaction mixture of isolated cells are used during the contacting. If desired, products obtained from the microorganisms can be used. Such products may be obtained by processing the cells. Suitable catalytic products include, for example, the cell homogenate, the cells treated with acetone, the immobilized cells, the extract from the cells, and the β-tyrosinase purified from the cell extract. When these products are used, the contacting is conducted in an aqueous solution.

According to the method of the present invention, the catalytic reaction is conducted at a temperature lower than 25° C., preferably at a temperature of from 5° to 20° C., in the presence of anhydrous crystals of L-DOPA. Crystal of L-DOPA which are formed as a result of the contacting step precipitate as anhydrous crystals from the reaction mixture. The thus-precipitated crystals can then be collected.

The pH of the contacting step is of from 7.5 to 9.0, preferably 7.7 to 8.7.

When the contacting step is conducted in the absence of anhydrous crystals of L-DOPA at temperatures below the boundary temperature of L-DOPA, that is about 25° C., the crystals which form, accumulate and precipitate in the reaction mixture at concentrations higher than the supersaturation solubility of L-DOPA are monohydrated crystals. Under similar condition but at temperatures higher than the boundary temperature, anhydrous crystals of L-DOPA are formed. The boundary temperature depends on the composition, the pH value, etc. of the reaction mixture.

Monohydrated crystals of L-DOPA have a small particle size, and they are difficult to precipitate in the reaction mixture and are de-watered extremely poorly. Therefore, even if such monohydrated crystals are desired to be directly separated and recovered as crude crystals from the reaction mixture by filtration, centrifugation or the like operation, the yield of the recovery is low and the recovered crystals contain a large amount of the mother liquid adhered thereto.

As opposed to monohydrate crystals, anhydrous crystals of L-DOPA have a large particle size, are easy to precipitate in the reaction mixture and are de-watered well. Therefore, they may directly be separated and recovered as crude crystals from the reaction mixture by simple operation such as filtration, centrifugation or the like, and the yield of the recovery is high. In addition, the recovered crystals contain only a small amount of the mother liquid adhered thereto.

Anhydrous crystals of L-DOPA recovered from the process of the present invention may be further purified by ordinary methods such as ion-exchange resin treatment, crystallization, etc.

Given these situations, a method may be considered suitable wherein the reaction is carried out at a temperature not lower than 25° C. so as to make anhydrous crystals of L-DOPA precipitated in the reaction mixture and thereafter separating and recovering the same from the reaction mixture. However, reaction temperatures not lower than 25° C. induces unfavorable side reactions by which the yield of L-DOPA is lowered. For this reason, temperatures lower than 25° C. are not favorable for industrial production of L-DOPA.

According to the present invention, the catalytic reaction is conducted at a temperature lower than 25° C. in the presence of anhydrous crystals of L-DOPA such that L-DOPA formed by the reaction is precipitated as anhydrous crystals in the reaction mixture. Accordingly, anhydrous crystals of L-DOPA are produced at a high yield by the method of the present invention.

As one means for attaining the condition where anhydrous crystals of L-DOPA are present in the reaction mixture, the reaction can be conducted at a temperature at which L-DOPA is formed and precipitated as monohydrated crystals in the reaction mixture and anhydrous crystals of L-DOPA are added to the reaction mixture.

The optimum temperature at which L-DOPA is formed and precipitated as monohydrated crystals in the reaction mixture is generally lower than 25° C., although some variation is present depending on the composition, the pH value, etc. of the reaction mixture. The uppermost limit of the temperature may easily be determined by experiments. If the reaction is continued at temperatures lower than 25° C. in the absence of anhydrous crystals of L-DOPA, monohydrated crystals of L-DOPA will precipitate in the reaction mixture. If, however, anhydrous crystals of L-DOPA are added as seed crystals to the reaction mixture prior to the precipitation of such monohydrated crystals of L-DOPA therein and the reaction is continued under these conditions, the L-DOPA formed will precipitate as anhydrous crystals in the reaction mixture.

The time when anhydrous crystals of L-DOPA are added to the reaction mixture is preferably after the start of the reaction and before the precipitation of monohydrated crystals of L-DOPA to be formed by the reaction. However, even after monohydrated crystals of L-DOPA have precipitated, they may often be converted into anhydrous crystals by polymorphic transition during the reaction, without causing any problems if a large amount of anhydrous crystals of L-DOPA exist in the reaction mixture.

The amount of the anhydrous crystals of L-DOPA to be added may be such that the anhydrous crystals added may exist as seed crystals in the reaction mixture, and this may be determined by experiments. As one example of the addition, 0.003 to 0.3 g/dl, preferably 0.03 g/dl of anhydrous crystals of L-DOPA are added to the reaction mixture at the time when 0.1 g/dl to 1.0 g/dl, preferably 0.3 g/dl of L-DOPA has been accumulated in the reaction mixture after the start of the reaction.

As another means for attaining the condition where anhydrous crystals of L-DOPA exist in the reaction mixture, mentioned is a method where the reaction is conducted at a temperature at which L-DOPA is formed and precipitated as anhydrous crystals in the reaction mixture whereby the reaction mixture may contain anhydrous crystals of L-DOPA therein. In this case, after the anhydrous crystals of L-DOPA have precipitated in the reaction mixture, the reaction temperature is lowered to a temperature lower than 25° C., preferably lower than 20° C., after which L-DOPA is generally precipitated as monohydrated crystals, and the reaction is continued at the lowered temperature. Even so, L-DOPA to be formed thereafter is precipitated as anhydrous crystals in the reaction mixture.

The temperature of the reaction when L-DOPA formed by the reaction is precipitated as anhydrous crystals also depends on the composition, the pH value, etc. of the reaction mixture, but it is generally not lower than 25° C. The lowermost limit of the temperature may easily be determined by experiments. In this case, if the reaction is continued without taking any particular means for varying the reaction temperature, L-DOPA to be formed will precipitate as anhydrous crystals but a large amount of other side products than L-DOPA will be formed so that the yield of L-DOPA is lowered. If, however, the reaction temperature is lowered to a temperature lower than 25° C., preferably lower than 20° C., after anhydrous crystals of L-DOPA have precipitated in the reaction mixture, and the reaction is continued under the condition, L-DOPA to be formed thereafter may be crystallized as anhydrous crystals in the reaction mixture since the previously precipitated anhydrous crystals act as seed crystals. Accordingly, the formation of side products may be prevented, and the anhydrous crystals of L-DOPA may be obtained at a high yield.

In carrying out the method of the present invention, it is recommended to add, either continuously or intermittently, an aqueous solution containing catechol to the reaction system in such an amount that the reaction system may have a catechol concentration of 1.0% or less, in order to prevent the reaction from being inhibited by the substrate at a high concentration. Due to the addition, the speed of forming L-DOPA is elevated and the amount of L-DOPA to be accumulated in the reaction system is increased, and therefore a more favorable result may be attained (see JP-A 5-123177).

If desired, a reducing agent such as sodium sulfite or cysteine and a chelating agent such as EDTA or citric acid may be added to the reaction system. The pH of the reaction mixture is suitably within the range of from 7.7 to 8.7, and the reaction time may be determined suitably, depending on the potency and the concentration of the β-tyrosinase source used and the concentration of the substrate used.

Anhydrous crystals of L-DOPA thus obtained according to the present invention precipitate in the reaction mixture and may well be de-watered. Therefore, they may easily be collected from the reaction mixture as crude crystals by filtration, swinging or the like operation, and the crude crystals may be further purified by ordinary methods, for example by treatment with ion-exchange resins, crystallization, etc.

EXAMPLES

Having generally described this invention, a further understanding can be obtained by reference to certain specific examples which are provided herein for purposes of illustration only and are not intended to be limiting unless otherwise specified.

Example 1

One platinum loop of cells of *Erwinia herbicola* (ATCC 21433) that had been incubated on a bouillon-agar medium at 31.5° C. for 24 hours were inoculated in 50 ml of a medium having the composition shown in Table 1 below (hereinafter referred to as a seed cultivation medium) that had been put in a 500 ml-shaking flask, and the shaking cultivation was conducted at 31° C. for 12 hours.

TABLE 1

| Components | Concentration (%) |
|---|---|
| Glycerol | 1 |
| $KH_2PO_4$ | 0.05 |
| $MgSO_4.7H_2O$ | 0.05 |
| $FeSO_4.7H_2O$ | 0.001 |
| $ZnSO_4.7H_2O$ | 0.001 |
| Fumaric Acid | 0.2 |
| L-tyrosine | 0.2 |
| Hydrolysate of Soybean Protein | 1.5 |
| Pyridoxine | 0.01 |
| pH 7.5 (KOH) | |

150 ml of the culture were transplanted in 3 liters of a medium having the composition shown in Table 2 below (hereinafter referred to as a main cultivation medium) that had been put in a 5 liter-jar fermenter, and the cultivation was conducted at 28° C. for 36 hours while the pH of the medium was kept at 7.5 by adding thereto ammonia gas and glucose.

TABLE 2

| Components | Concentration |
|---|---|
| Glycerol | 0.5 |
| $KH_2PO_4$ | 0.05 |
| $MgSO_4.7H_2O$ | 0.05 |
| $FeSO_4.7H_2O$ | 0.001 |
| $ZnSO_4.7H_2O$ | 0.001 |
| Fumaric Acid | 0.7 |
| L-tyrosine | 0.2 |
| Glycine | 0.3 |
| DL-alanine | 0.3 |
| DL-methionine | 0.1 |
| L-phenylalanine | 0.2 |
| Sodium L-glutamate | 0.55 |
| Hydrolysate of Soybean Protein | 1.0 |
| Pyridoxine | 0.01 |
| De-foaming Agent | 0.002 |
| pH 7.5 (KOH) | |

After the cultivation, the culture was divided into parts of 400 ml each. The parts were separately subjected to centrifugation to recover the cells therefrom. The thus-recovered cells were added to 300 ml of a reaction mixture for producing L-DOPA that had the composition shown in Table 3 below (hereinafter referred to as a reaction mixture) and reacted at 10° C., 15° C., 20° C., 25° C., 30° C., separately. During the reaction, an aqueous solution containing 20% of catechol and 20% of sodium pyruvate was continuously added to the reaction system so that the catechol concentration in the reaction system was kept at 0.5% or less.

TABLE 3

| Components | Concentration (%) |
|---|---|
| Sodium Pyruvate | 1.5 |
| Catechol | 1.0 |
| Ammonium Chloride | 4.0 |
| Ammonium Nitrate | 0.1 |
| Sodium Sulfite | 0.2 |
| EDTA | 0.3 |
| pH 8.0 (aqueous ammonia) | |

After reacted for 16 hours, the amount of L-DOPA formed was measured. Table 4 below shows the amount of L-DOPA formed and the crystal morphology of the crystals of L-DOPA precipitated.

TABLE 4

| Reaction Temperature (°C.) | Amount of L-DOPA Accumulated (g/dl) | Morphology of Crystals | Yield (% by mol) to Catechol |
|---|---|---|---|
| 10 | 9.0 | Monohydrated Crystals | 85 |
| 15 | 10.0 | Monohydrated Crystals | 85 |
| 20 | 9.5 | Monohydrated Crystals | 75 |
| 25 | 7.0 | Anhydrous Crystals | 60 |
| 30 | 3.0 | Anhydrous Crystals | 20 |

Example 2

One platinum loop of cells of *Erwinia herbicola* (ATCC 21433) that had been incubated on a bouillon-agar medium at 31.5° C. for 24 hours were inoculated in 50 ml of a seed cultivation medium having the composition mentioned above that had been put in a 500 ml-shaking flask, and the shaking cultivation was conducted at 31° C. for 12 hours. 150 ml of the culture were transplanted in 3 liters of a main cultivation medium having the composition mentioned above that had been put in a 5 liter-jar fermenter, and the cultivation was conducted at 28° C. for 36 hours while the pH of the medium was kept at 7.5 by adding thereto ammonia gas and glucose. After the cultivation, the culture was divided into parts of 400 ml each. The parts were separately subjected to centrifugation to recover the cells therefrom. The thus-recovered cells were added to 300 ml of a reaction mixture having the composition mentioned above, and reacted at 15° C. while anhydrous crystals of L-DOPA were added thereto at the start of the reaction and 0. 5, 1, 2, 4 and 6 hours after the start of the reaction, separately, each in an amount of 0.3 g/dl. During the reaction, an aqueous solution containing 20% of catechol and 20% of sodium pyruvate was continuously added to the reaction system so that the catechol concentration in the system was kept at 0.5% or less.

After reacted for 16 hours, the amount of L-DOPA formed was measured to be 10 g/dl in all of the reaction batches. Table 5 below shows the amount of L-DOPA accumulated in the reaction mixture at the indicated time when anhydrous crystals of L-DOPA had been added to the reaction mixture as well as the morphology of the final crystals of L-DOPA formed at the end of the reaction.

TABLE 5

| Time of addition of anhydrous crystals (hr) | Amount of L-DOPA accumulated (g/dl) | Morphology of final crystals |
|---|---|---|
| 0 | 0 | anhydrous crystals |
| 0.5 | 0.3 | anhydrous crystals |
| 1.0 | 1.2 | anhydrous crystals |
| 2.0 | 2.2 | monohydrated crystals + anhydrous crystals |
| 4.0 | 3.7 | monohydrated crystals + anhydrous crystals |
| 6.0 | 4.8 | monohydrated crystals + anhydrous crystals |
| (not added) | — | monohydrated crystals |

Example 3

One platinum loop of cells of *Erwinia herbicola* (ATCC 21433) that had been incubated on a bouillon-agar medium at 31.5° C. for 24 hours were inoculated in 50 ml of a seed cultivation medium having the composition mentioned above that had been put in a 500 ml-shaking flask, and the shaking cultivation was conducted at 31° C. for 12 hours. 150 ml of the culture were transplanted in 3 liters of a main cultivation medium having the composition mentioned above that had been put in a 5 liter-jar fermenter, and the cultivation was conducted at 28° C. for 36 hours while the pH of the medium was kept at 7.5 by adding thereto ammonia gas and glucose. After the cultivation, the culture was divided into two parts of 400 ml each. The both parts were separately subjected to centrifugation to recover the cells therefrom. The thus-recovered cells were added to 300 ml of a reaction mixture having the composition mentioned above, and reacted at 25° C. During the reaction, an aqueous solution containing 20% of catechol and 20% of sodium pyruvate was continuously added to the reaction system so that the catechol concentration in the system was kept at 0.5% or less. With the proceeding of the reaction, L-DOPA began to precipitate as anhydrous crystals. In one reaction batch of the two, the reaction temperature was lowered to 15° C. after anhydrous crystals of L-DOPA began to precipitate and the reaction was continued at the lowered temperature. In the other reaction batch, the reaction was continued still at 25° C. even after anhydrous crystals of L-DOPA began to precipitate.

After 16 hours, anhydrous crystals of L-DOPA were finally obtained in the both reaction batches. In the former batch where the reaction temperature was lowered, the yield of the product was 9.5 g/dl. In the latter batch where the reaction temperature was not lowered, however, the yield of the product was 7.0 g/dl. The yield of the product to catechol was 80% in the former batch, while that to catechol was 60% in the latter batch.

Example 4

One platinum loop of cells of *Erwinia herbicola* (ATCC 21433) that had been incubated on a bouillon-agar medium at 31.5° C. for 24 hours were inoculated in 50 ml of a seed cultivation medium having the composition mentioned above that had been put in a 500 ml-shaking flask, and the shaking cultivation was conducted at 31° C. for 12 hours. 25 ml of the culture were transplanted in 25 liters of a seed cultivation medium having the composition mentioned above that had been put in a 50 liter-jar fermenter, cultured therein at 31° C. for 16 hours, then transplanted in 500 liters of a main cultivation medium having the composition mentioned above that had been put in a 800 liter-jar fermenter, and further cultured therein at 28° C. for 36 hours while the pH of the medium was kept at 7.5 by adding thereto ammonia gas and glucose. After the cultivation, the cells were recovered from the culture by centrifugation, and they were divided into two parts. Each part was added to 200 liters of a reaction mixture having the composition mentioned above, and reacted at 15° C. During the reaction, an aqueous solution containing 20% of catechol and 20% of sodium pyruvate was continuously added to the reaction system so that the catechol concentration in the system was kept at 0.5% or less. To one reaction batch of the two, added were anhydrous crystals of L-DOPA in an amount of 0.5 g/dl when the concentration of L-DOPA formed and accumulated in the reaction system reached 0.3 g/dl after the start of the reaction, and the reaction was continued further. To the other reaction batch, anhydrous crystals of L-DOPA were not added and the reaction was continued further. After 20 hours, the amount of L-DOPA formed was 10.0 g/dl in both of the two reaction batches. Anhydrous crystals of L-DOPA precipitated in the former reaction batch, while monohydrated crystals of L-DOPA formed in the latter reaction batch. The crystals formed were separated from 200 liters of each of the two reaction batches, using Sharpless Superdecanter P660 Model (made by Tomoe Industrial Co.), and slurries of crude crystals were recovered. The recovery of L-DOPA from the former reaction batch where anhydrous crystals of L-DOPA had precipitated was 96%, and the water content in the slurry of crude crystals recovered was 26%. However, the recovery of L-DOPA from the latter reaction batch where monohydrated crystals of L-DOPA had formed was only 28%, and the slurry of crude crystals recovered contained 63% of water. One kg of the slurry of crude crystals of L-DOPA that had been recovered as anhydrous crystals was dissolved in an acid to remove the cells therefrom by an ordinary method, and the crystals were adsorbed to active charcoal in a column and then eluted with a dilute aqueous ammonia containing 0.2% of sodium sulfite. After neutralized and concentrated, the eluate was recrystallized three times each with water. Thus, 350 g of pure crystals of L-DOPA were obtained.

What is claimed as new and is desired to be secured by Letters Patent of the United States is:

1. A method for producing anhydrous crystals of L-3,4-dihydroxyphenylalanine (L-DOPA), comprising:
    a) contacting a microorganism of *Erwinia herbicola* having β-tyrosinase activity with catechol, pyruvic acid and ammonium ion or with catechol and L-serine at a temperature lower than 25° C. in a reaction mixture and in the presence of anhydrous crystals of L-DOPA, which are added to said reaction mixture after commencing said reaction and before precipitation of monohydrated crystals of L-DOPA;
    b) precipitating anhydrous crystals of L-DOPA from said reaction mixture; and
    c) collecting said precipitated anhydrous crystals.

2. The method of claim 1, wherein said microorganism is selected from the group consisting of *Erwinia herbicola* ATCC 21433 and *Erwinia herbicola* ATCC 21434.
3. The method of claim 1, wherein said ammonium ion is from an ammonium salt selected from the group consisting of ammonium acetate, ammonium chloride, ammonium sulfate, ammonium nitrate, ammonium phosphate and an ammonium salt of an organic acid.
4. The method of claim 3, wherein said ammonium salt is ammonium chloride.
5. The method of claim 1, wherein said step a) is effected at from 5° to 20° C.
6. The method of claim 1, wherein said step a) is conducted at a pH of from 7.5 to 9.0.
7. The method of claim 6, wherein said step a) is conducted at a pH of from 7.7 to 8.7.
8. The method of claim 1, wherein said microorganism comprises 1 to 10% of the weight of the reaction mixture.
9. The method of claim 1, wherein about 0.003 to 0.3 g/dl of anhydrous crystals of L-DOPA are added to said reaction mixture when 0.1 g/dl to 1.0 g/dl of L-DOPA has accumulated in the reaction mixture after starting the reaction.
10. A method for producing anhydrous crystals L-3,4-dihydroxyphenylalanine (L-DOPA), comprising:
    a) contacting a microorganism of *Erwinia herbicola* having β-tyrosinase activity with catechol, pyruvic acid and ammonium ion or with catechol and L-serine at a temperature greater than or equal to about 25° C. in a reaction mixture;
    b) precipitating L-DOPA formed as a result of said contacting as anhydrous crystals in the reaction mixture;
    c) lowering the temperature of the reaction mixture to a temperature of lower than 25° C., after precipitating said anhydrous crystals of L-DOPA;
    d) continuing to precipitate L-DOPA formed anhydrous crystals from the reaction mixture; and
    e) collecting precipitated anhydrous crystals of L-DOPA.
11. The method of claim 10, wherein said microorganism is selected from the group consisting of *Erwinia herbicola* ATCC 21433 or *Erwinia herbicola* ATCC 21434.
12. The method of claim 11, wherein said ammonium ion is from an ammonium salt selected from the group consisting of ammonium acetate, ammonium chloride, ammonium sulfate, ammonium nitrate, ammonium phosphate and an ammonium salt of an organic acid.
13. The method of claim 12, wherein said ammonium salt is ammonium chloride.
14. The method of claim 10, wherein said step c) is effected at lower than 20° C.
15. The method of claim 10, wherein said step a) is conducted at a pH of from 7.5 to 9.0.
16. The method of claim 15, wherein said step a) is conducted at a pH of from 7.7 to 8.7.
17. The method of claim 10, wherein said microorganism comprises 1 to 10% of the weight of the reaction mixture.

* * * * *